(12) United States Patent
Sawasaki et al.

(10) Patent No.: US 9,310,380 B2
(45) Date of Patent: Apr. 12, 2016

(54) METHOD FOR ANALYZING PROTEINS CONTRIBUTING TO AUTOIMMUNE DISEASES, AND METHOD FOR TESTING FOR SAID DISEASES

(75) Inventors: Tatsuya Sawasaki, Matsuyama (JP); Yaeta Endo, Matsuyama (JP); Tomoaki Ishigami, Yokohama (JP); Ichiro Aoki, Yokohama (JP)

(73) Assignees: National University Corporation Ehime University, Matsuyama-shi, Ehime (JP); Public University Corporation Yokohama City University, Yokohama-shi, Kanagawa (JP)

( * ) Notice: Subject to any disclaimer, the term of this patent is extended or adjusted under 35 U.S.C. 154(b) by 0 days.

(21) Appl. No.: 13/988,269

(22) PCT Filed: Nov. 16, 2011

(86) PCT No.: PCT/JP2011/076450
§ 371 (c)(1),
(2), (4) Date: Jun. 26, 2013

(87) PCT Pub. No.: WO2012/067165
PCT Pub. Date: May 24, 2012

(65) Prior Publication Data
US 2013/0273579 A1    Oct. 17, 2013

(30) Foreign Application Priority Data
Nov. 17, 2010    (JP) .................... 2010-256418

(51) Int. Cl.
*G01N 33/53*    (2006.01)
*G01N 33/564*    (2006.01)
*G01N 33/68*    (2006.01)

(52) U.S. Cl.
CPC .......... *G01N 33/6869* (2013.01); *G01N 33/564* (2013.01); *G01N 33/6845* (2013.01); *G01N 2800/323* (2013.01)

(58) Field of Classification Search
CPC ... C07K 14/435; A61K 38/17; A61K 38/177; A61K 49/0008; G01N 33/57484; G01N 33/68; G01N 2333/99; G01N 2800/042; G01N 33/573; G01N 33/53; G01N 33/6845; G01N 33/6872; G01N 2510/00; G01N 2800/56
See application file for complete search history.

(56) References Cited

U.S. PATENT DOCUMENTS

2007/0190579 A1 *   8/2007   Endo et al. ............. 435/7.5
2008/0254482 A1 *  10/2008   Mattoon et al. ......... 435/7.1

FOREIGN PATENT DOCUMENTS

| WO | WO 2005/100405 | 10/2005 |
|---|---|---|
| WO | WO 2007/015128 | 2/2007 |
| WO | WO 2008/013914 | 1/2008 |

OTHER PUBLICATIONS

Soltesz et al., (Arthiritis & Therapy 2010, May 6, vol. 12: R78).*
Wiesmann et al., (Clin Chem 1993; 39/12, pp. 2492-2494).*
Stampfer et al., Circulation 2004, 1909:IV3-IV-5.*
Matsuoka et al., (Journal of Proteome Research, Jun. 2010, vol. 9, pp. 4264-4273).*
Blassi et al. (Atheroclerosis 2008;201:17-32).*
Sawasaki et al., (Phytochemistry 65 (2004) 1549-1555).*
Binder,C.J. et al., "The role of natural antibodies in atherogenesis," J. Lipid Res., 2005, vol. 46, No. 7, p. 1353-1363.
Masato Nose et al., "Nanchisei Kekkan'en ni Kansuru Chosa Kenkyu Musaibo Tanpakushitsu Goseikei ni yoru Jiko Kotai no Screening-ho to Kanben na ELISA-ho no Kakuritsu," Nanchisei Kekkan'en ni Kansuru Chosa Kenkyu Heisei 19 Nendo Sokatsu Buntan Kenkyu Hokokusho, 2008, pp. 53 to 56, Translation provided.

* cited by examiner

*Primary Examiner* — Shafiqul Haq
*Assistant Examiner* — Carmencita M Belei
(74) *Attorney, Agent, or Firm* — Don D. Cha; Hamilton DeSanctis & Cha, LLP.

(57) ABSTRACT

Provided are a detection method for a myriad of proteins involved in an autoimmune disease with high sensitivity and high efficiency, and an analysis method for data resulting from the detection method. In order to construct the detection method and analysis method, there is provided means for comprehensively analyzing the proteins involved in an autoimmune disease by bringing a mammal-derived protein expressed in a cell-free protein synthesis system into contact with a sample derived from a patient with an autoimmune disease to detect autoantibody production, and subjecting the detected data to statistical analysis processing, and further, gene ontology analysis and/or pathway analysis.

2 Claims, 14 Drawing Sheets

⊞ ▣ GO:0008150 : biological_process [270820 gene products]
  ⊞ ▣ GO:0051234 : establishment of localization [32387 gene products]
    ⊞ ▣ GO:0006810 : transport [32056 gene products]
      ⊞ ▣ GO:0015837 : amine transport [1637 gene products]
        ⊞ ▣ GO:0006865 : amino acid transport [1272 gene products]
      ⊞ ▣ GO:0015849 : organic acid transport [1835 gene products]
        ⊞ ▣ GO:0046942 : carboxylic acid transport [1811 gene products]
          ⊞ ▣ GO:0006865 : amino acid transport [1272 gene products]
  ⊞ ▣ GO:0051179 : localization [36381 gene products]
    ⊞ ● GO:0051234 : establishment of localization [32387 gene products]
      ⊞ ▣ GO:0006810 : transport [32056 gene products]
        ⊞ ▣ GO:0015837 : amine transport [1637 gene products]
          ⊞ ▣ GO:0006865 : amino acid transport [1272 gene products]
        ⊞ ▣ GO:0015849 : organic acid transport [1835 gene products]
          ⊞ ▣ GO:0046942 : carboxylic acid transport [1811 gene products]
            ⊞ ▣ GO:0006865 : amino acid transport [1272 gene products]

FIGURE 1

⊞ ▦ GO:0015837 : amine transport [1637 gene products]
  ⊟ ▦ GO:0006865 : amino acid transport [1272 gene products]
    ⊞ ▦ GO:0015800 : acidic amino acid transport [95 gene products]
    ⊞ ▦ GO:0032973 : amino acid export [12 gene products]
    ⊞ ▦ GO:0043090 : amino acid import [44 gene products]
    ⊞ ▦ GO:0003333 : amino acid transmembrane transport [8 gene products]
    ⊞ ▦ GO:0015801 : aromatic amino acid transport [16 gene products]
    ⊞ ▦ GO:0015802 : basic amino acid transport [81 gene products]
    ⊞ ▦ GO:0015803 : branched-chain aliphatic amino acid transport [133 gene products]
    ⊞ ▦ GO:0015879 : carnitine transport [27 gene products]
    ⊞ ▦ GO:0015881 : creatine transport [3 gene products]
    ⊞ ▦ GO:0042940 : D-amino acid transport [26 gene products]
    ⊞ ▦ GO:0006860 : extracellular amino acid transport [1 gene product]
    ⊞ ▦ GO:0015884 : folic acid transport [15 gene products]
    ⊞ ▦ GO:0031460 : glycine betaine transport [3 gene products]
    ⊞ ▦ GO:0015807 : L-amino acid transport [150 gene products]
    ⊞ ▼ GO:0051956 : negative regulation of amino acid transport [7 gene products]
    ⊞ ▦ GO:0015804 : neutral amino acid transport [169 gene products]
    ⊞ ▦ GO:0015822 : ornithine transport [21 gene products]
    ⊞ ⬥ GO:0051957 : positive regulation of amino acid transport [9 gene products]
    ⊞ ▦ GO:0051955 : regulation of amino acid transport [22 gene products]
    ⊞ ▦ GO:0000101 : sulfur amino acid transport [36 gene products]
    ⊞ ▦ GO:0034487 : vacuolar amino acid transport [13 gene products]

FIGURE 2

| HsSYMBOL | Function |
|---|---|
| SLC36A4 | solute carrier family 36 (proton/amino acid symporter), member 4. mRNA (cDNA clone MGC:48630) |
| SLC7A9 | solute carrier family 7 (cationic amino acid transporter, y+ system), member 9, mRNA (cDNA clone MGC:24085) |
| SLC1A3 | solute carrier family 1 (glial high affinity glutamate transporter), member 3, mRNA (cDNA clone MGC:41861) |
| SLC7A11 | solute carrier family 7 (cationic amino acid transporter, y+ system), member 11, mRNA (cDNA clone MGC:20026) |

FIGURE 3

| Hub Gene | attribute | 1 | 2 | 3 | 4 | 5 | 6 | 7 | 8 | 9 | 10 | 11 |
|---|---|---|---|---|---|---|---|---|---|---|---|---|
| PIN1 | severity | CSNK2A1 association | GSK3B activation | IL5 inhibition | PCNA association | | | | | | | |
| STX1A | mild | SYT1 association | VAMP2 inhibition | VAPA association | STX4 association | IL5 activation | STX3 association | CSNK2A1 activation | EIF4E activation | | | |
| CSNK2A1 | positive upper | STX1A activation | HNRNPA2B1 activation | STX4 activation | GSK3B association | NPM1 activation | HMGN1 activation | TUBB activation | SRPK1 activation | PIN1 association | KLF1 association | EIF2S2 association |
| VAMP2 | positive upper | STX1A inhibition | PRKCZ activation | RABAC1 association | HRB association | VAMP8 association | STX4 inhibition | VAPA regulation | | | | |
| GSK3B | positive upper | PRKCZ inhibition | PHF1 association | RPS15 regulation | CCND2 regulation | IL5 inhibition | PIN1 activation | CSNK2A1 association | | | | |
| CCND2 | positive upper | GSK3B regulation | FKBP4 inhibition | OPRS1 regulation | CDK5R1 regulation | PCNA association | IL5 association | | | | | |
| PCNA | positive upper | HIST1H1C activation | FUS activation | AKTIP inhibition | NPM1 association | CCND2 association | KCTD13 association | TGM2 inhibition | PIN1 association | FZR1 regulation | | |
| IL5 | positive medium | STX1A activation | PRKCZ inhibition | GSK3B inhibition | CCND2 association | CYSLTR1 activation | PTAFR association | CRISP2 activation | PIN1 inhibition | | | |

FIGURE 4

|  | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| Cluster1 | ZDHHC17 | ABCF1 | POLH | DTX3L | KCTD13 | KIAA0409 | RNF33 | MAP1LC3B | SLC1A3 | PRPF3 | TAF11 | CENTA2 | FAM32A | SRPK2 | ZNF625 |
| Cluster2 | PIN1 | MRPL38 | CCDC68 | TUBB | SLC44A5 | TMEM55A | KIF19 | ZNF9 | CAPN9 | MLC1 | SLC17A3 | RPS10 | DDX39 | QPRS1 | ZNF200 |
| Cluster3 | ITGB1BP1 | RPL27A | SLCO4A1 | EBI2 | SAFB2 | ZNF668 | FZR1 | FATE1 | HSP2BP | IFIT2 | MNS1 | CDK5R1 | REDQL | GALNT4 | SMAD5 |
| Cluster4 | CCNI2 | AYTL1 | LGALS8 | HTR2B | AEBP3 | DNAJB14 | TMEM23 | RPL37A | RSBN1 | PARK2 | KIFAP3 | STX4A | ZNF193 | ZNF215 | SRPK1 |
|  | 16 | 17 | 18 | 19 | 20 | 21 | 22 | 23 | 24 | 25 | 26 | 27 | 28 | 29 | 30 |
| Cluster1 | TMEM31 | DTNA | REM34 | MSL3L1 | VIL1 | JSRP1 | GADYBP | LYSMD1 | SAF30BP | GPM6A | PHF1 | UBXD3 | C15orf33 | H1FX | GNL1 |
| Cluster2 | H2AFZ | TGM2 | NARF | NFM3 | MGLL | NDST1 | ALOX5AP | TMEM16K | WDR69 | KLHL3 | OLFML3 | PMM2 | FABP6 | DCN | FCRL2 |
| Cluster3 | KLHL12 | HIST2H2AC | CDC108 | C13orf7 | KCNJ12 | TNFAIP8L2 | MRPS6 | RG9MTD2 | NHP2L1 | NPY1R | KPNA1 | RFX5 | TMIST2 | HMGN4 | SNRPD2 |
| Cluster4 | SEC61A2 | EIF2S6 | STK11IP | P2RY14 | SPDCK1 | GARPA | TRIM45 | ADM1B | REL2 | CORT | DDX6B1 | LOXHD1 | CRI8P2 | THOP1 | C13orf6 |
|  | 31 | 32 | 33 | 34 | 35 | 36 | 37 | 38 | 39 | 40 | 41 | 42 | 43 | 44 | 45 |
| Cluster1 | ZMAT2 | SLC7A3 | CACNE1 | RPL36 | FKBP4 | TRIP10 | NOL1 | RPL7L1 | PRKX2 | HIST1H10 | EMG1 | RNF10 | SRPF13 | RDX | C1orf63 |
| Cluster2 | ATP6V1B2 | MADA | RABAC1 | EFTUD2 | SHD | REEP2 | CPO | TUFT1 | TMEM101 | CYP46A1 | SYT4 | MFAP3 | APH1B | C10orf65 | GABRA3 |
| Cluster3 | SP110 | EIF4E2 | RIT2 | EAT4 | ALS2CR11 | HIST1H2BK | ENPP5 | RG9MTD2 | B4GALT1 | MARCH8 | EIF2S2 | TMEM103 | LGTN | RFP2 | MAST2 |
| Cluster4 | LRRC56 | PARN | MANSC1 | SETD4 | BCAS2 | NBPF3 | HER3 | KCNK1 | PDNA | MORN1 | RABL3 | RABL3 | RGS7 | SPSB3 | CFLAR |
|  | 46 | 47 | 48 | 49 | 50 | 51 | 52 | 53 | 54 | 55 | 56 | 57 | 58 | 59 | 60 |
| Cluster1 | C12orf52 | NUMB | BTBD10 | KGTD14 | PLEKHA1 | SLC36A4 | HIST1H2AA | CLDN3 | RFX2 | SYT2B | PVRL3 | NOX4 | C1orf57 | CHRM5 | HOMER1 |
| Cluster2 | PDE6D | LRRC39 | BGGALT3 | KCTD13 | GSK3B | PTGDS | STX1A | TPST1 | GAD1 | SLCO1C1 | AKAP3 | PTAFR | P2RY10 | PPP1R3C | C1orf65 |
| Cluster3 | RNF128 | VIL2 | ANKRD5 | EPS8 | JAKMIP1 | RPL10A | SMAP1 | ZNF24 | THEG | SLCO3A1 | IGSF6 | HNRPR | NARS | DDX2 | C19orf34 |
| Cluster4 | DDP1B | ACTA1 | RAP2A | D2IP1 | NDUFS1 | ZNF92 | MRPS19A | C1orf62 | FTPRN | GNPTG | LPGAT1 | KLHL26 | PARVA | SLC43A3 | PRNP |
|  | 61 | 62 | 63 | 64 | 65 | 66 | 67 | 68 | 69 | 70 | 71 | 72 | 73 | 74 | 75 |
| Cluster1 | VPS41 | PPP3K2B | PRKCZ | EIF2S4 | GABARAPL2 | KLF1 | DUSP12 | HIST1H4C | SGDM1 | ING4 | CLUS | FUSIP1 | ZFYVE17 | MFAP1 | RNF182 |
| Cluster2 | MT1G | ASNA1 |  |  |  |  |  |  |  |  |  |  |  |  |  |
| Cluster3 | TNF1 | ZNF435 | HIST1H4I | ZNF207 | DYB5R2 | LRRC49 | RPL37A | ZNF84 | YAFA | TMEM74 | DDX49 | WDR47 | VAMP4 | PEA15 | C1orf62 |
| Cluster4 | SUMO2 | ST6GALNAC1 | CCDC11 | IL5 | ZNF578 |  |  |  |  |  |  |  |  |  |  |

FIGURE 6

|  | 76 | 77 | 78 | 79 | 80 | 81 | 82 | 83 | 84 | 85 | 86 | 87 | 88 | 89 | 90 |
|---|---|---|---|---|---|---|---|---|---|---|---|---|---|---|---|
| Cluster1 | SYT1 | TMEM17 | LRRC34 | S100A16 | SYK | ZNF165 | C19orf6 | STX3A | CDH19 | VPS37A | H2AFJ | UCP3 | BCAP29 | RAG1AP1 | CHCHD6 |
| Cluster2 |  |  |  |  |  |  |  |  |  |  |  |  |  |  |  |
| Cluster3 | SPATA5 | C2orf25 | HMGN1 | NUP35 | SAMHD1 | MSH4 | KCNJ8 | USP15 | RPS13 | TEKT4 | FTS | EIF3S5 | ITM2A | FBXO2 | LHFPL5 |
| Cluster4 |  |  |  |  |  |  |  |  |  |  |  |  |  |  |  |

|  | 91 | 92 | 93 | 94 | 95 | 96 | 97 | 98 | 99 | 100 | 101 | 102 | 103 | 104 | 105 |
|---|---|---|---|---|---|---|---|---|---|---|---|---|---|---|---|
| Cluster1 | TRAK2 | RHCG | CHRNA7 | CMTM8 | RSPO3 | SLC37A4 | ACE | GPSN2 | USP10 | DDX47 | TIGD1 | HIGD2A | DDX7C | SFRS3 | FUT11 |
| Cluster2 |  |  |  |  |  |  |  |  |  |  |  |  |  |  |  |
| Cluster3 | ELOF1 | HIST1H4E | SLC30A3 | C1orf85 | S100A13 | EIF4E | SLC30A4 | C21orf5 | PSRC1 | CCDC28B | VAMP2 | PTPLA | ORC6L | HIST1H2BJ | ATP6V1G1 |
| Cluster4 |  |  |  |  |  |  |  |  |  |  |  |  |  |  |  |

|  | 106 | 107 | 108 | 109 | 110 | 111 | 112 | 113 | 114 | 115 | 116 | 117 | 118 | 119 | 120 |
|---|---|---|---|---|---|---|---|---|---|---|---|---|---|---|---|
| Cluster1 | SLC7A11 | BIRC5 | ENPP2 | NEURL | CYBA | CALM2 | GPR17 | SLC6A13 | DGAT2 | GDPD1 | LUZP1 | RTP4 | DNAJC15 | CDKL3 | PLEKHB1 |
| Cluster2 |  |  |  |  |  |  |  |  |  |  |  |  |  |  |  |
| Cluster3 | RAD51AP1 | RPS15 | HIST4H4 | LRRC6 | FUS | CXXC5 | PPFIBP2 | ZNF439 | HMG20B | CSNK2A1 | TOMM34 | CYSLTR1 | TNFRSF10B | RPL17 | NPM1 |
| Cluster4 |  |  |  |  |  |  |  |  |  |  |  |  |  |  |  |

|  | 121 | 122 | 123 | 124 | 125 | 126 | 127 | 128 | 129 |
|---|---|---|---|---|---|---|---|---|---|
| Cluster1 | ACAT2 | PRND | PCP2 | FIS1 | ARHGEF7 | PHF13 |  |  |  |
| Cluster2 |  |  |  |  |  |  |  |  |  |
| Cluster3 | STK33 | PLEK2 | IMPACT | HKR3 | METTL1 | HNRPA2B1 | CATSPER1 | DGCR8L | VAMP8 |
| Cluster4 |  |  |  |  |  |  |  |  |  |

FIGURE 7

| HsSYMBOL | Ha-1 | Ha-2 | Ha-3 | Ha-4 |
|---|---|---|---|---|
| GABARAPL2 | 18.8 | 11.2 | 9.9 | 11.0 |
| SRP19 | 20.3 | 9.8 | 6.9 | 7.1 |
| SMAP1 | 2.5 | 1.8 | 1.7 | 5.2 |
| MAP1LC3B | 27.9 | 13.9 | 6.2 | 5.0 |
| ZNF668 | 4.2 | 3.3 | 3.3 | 4.9 |
| SAFB2 | 4.1 | 2.8 | 2.5 | 4.7 |
| LGTN | 2.3 | 2.3 | 2.0 | 3.3 |
| H1FX | 8.5 | 5.8 | 2.4 | 2.9 |
| CACYBP | 4.7 | 3.4 | 2.4 | 2.6 |
| PIP5K2B | 5.0 | 2.9 | 2.0 | 2.6 |
| PCNA | 2.2 | 2.0 | 2.9 | 2.5 |
| RBM34 | 7.1 | 3.9 | 2.0 | 2.4 |
| C1orf63 | 6.6 | 3.3 | 2.1 | 2.4 |
| JSRP1 | 6.1 | 3.9 | 1.9 | 2.4 |
| KLF1 | 3.8 | 2.3 | 2.0 | 2.3 |

FIGURE 8

| | Cluster1 | | | | | |
|---|---|---|---|---|---|---|
| | GOID | Pvalue | ExpCount | Count | Size | Term |
| Amino acid transporter | GO:0006865 | 0.013 | 1.873 | 4 | 4 | amino acid transport |
| | GO:0015849 | 0.013 | 1.873 | 4 | 4 | organic acid transport |
| | GO:0051606 | 0.040 | 1.030 | 3 | 3 | detection of stimulus |
| | GO:0005886 | 0.011 | 21.745 | 30 | 53 | plasma membrane |
| | GO:0005275 | 0.013 | 1.364 | 4 | 4 | amine transmembrane transporter activity |
| | GO:0015179 | 0.013 | 1.364 | 4 | 4 | L-amino acid transmembrane transporter |

| | Cluster2 | | | | | |
|---|---|---|---|---|---|---|
| | GOID | Pvalue | ExpCount | Count | Size | Term |
| Inflammation response, Carbohydrate metabolism Steroid metabolism | GO:0044262 | 0.004 | 1.299 | 5 | 8 | cellular carbohydrate metabolic process |
| | GO:0006954 | 0.006 | 1.948 | 6 | 12 | inflammatory response |
| | GO:0006629 | 0.014 | 2.273 | 6 | 14 | lipid metabolic process |
| | GO:0009605 | 0.029 | 2.598 | 6 | 16 | response to external |
| | GO:0008202 | 0.032 | 0.812 | 3 | 5 | steroid metabolic process |
| | GO:0044425 | 0.019 | 20.806 | 28 | 129 | membrane part |
| | GO:0016021 | 0.028 | 18.226 | 25 | 113 | integral to membrane |

| | Cluster3 | | | | | |
|---|---|---|---|---|---|---|
| | GOID | Pvalue | ExpCount | Count | Size | Term |
| Translation, transcription, recombination | GO:0006310 | 0.012 | 1.343 | 4 | 4 | DNA recombination |
| | GO:0006413 | 0.012 | 1.343 | 4 | 4 | translational initiation |
| | GO:0032774 | 0.021 | 10.745 | 16 | 32 | RNA biosynthetic process |
| | GO:0006350 | 0.036 | 11.753 | 17 | 35 | transcription |
| | GO:0005840 | 0.027 | 4.235 | 8 | 13 | ribosome |
| | GO:0003677 | 0.003 | 15.256 | 24 | 46 | DNA binding |
| | GO:0003723 | 0.006 | 6.936 | 13 | 22 | RNA binding |

| | Cluster4 | | | | | |
|---|---|---|---|---|---|---|
| | GOID | Pvalue | ExpCount | Count | Size | Term |
| RNA catabolism | GO:0000184 | 0.026 | 0.325 | 2 | 2 | mRNA catabolic process, nonsense-mediated decay |
| | GO:0006401 | 0.026 | 0.325 | 2 | 2 | RNA catabolic process |

FIGURE 10

* p<0.01 vs Full constructs of IL5

Legends:

Full = Full length IL-5 (SEQ ID NO:1)

20-135 = IL-5 (20-135) (SEQ ID NO:2)

64-135 = IL-5 (64-135) (SEQ ID NO:3)

RECEIVER OPERATING CHARACTERISTIC CURVE (ROC CURVE) AND
SENSITIVITY SPECIFICITY OF ANTI-IL-5 ANTIBODY TITER

A

| cut off v. | FPF | TPF |
|---|---|---|
| 1.25 | 0 | 0.7625 |
| 1.24 | 0 | 0.7625 |
| 1.23 | 0.1 | 0.775 |
| 1.22 | 0.1 | 0.7875 |
| 1.21 | 0.1 | 0.8125 |
| 1.2 | 0.1 | 0.8125 |
| 1.19 | 0.1 | 0.8125 |
| 1.18 | 0.3 | 0.825 |
| 1.17 | 0.4 | 0.825 |
| 1.16 | 0.4 | 0.85 |
| 1.15 | 0.4 | 0.85 |
| 1.14 | 0.4 | 0.8625 |
| 1.13 | 0.4 | 0.875 |
| 1.12 | 0.5 | 0.875 |
| 1.11 | 0.5 | 0.8875 |
| 1.1 | 0.5 | 0.8875 |
| 1.09 | 0.5 | 0.8875 |
| 1.08 | 0.5 | 0.8875 |
| 1.07 | 0.6 | 0.9125 |
| 1.06 | 0.7 | 0.9125 |
| 1.05 | 0.7 | 0.9125 |
| 1.04 | 0.7 | 0.9125 |
| 1.03 | 0.7 | 0.9375 |
| 1.02 | 0.7 | 0.95 |
| 1.01 | 0.9 | 0.9625 |
| 1.00 | 1 | 0.9625 |

B

AUC=0.7971±0.0267

METHOD FOR ANALYZING PROTEINS CONTRIBUTING TO AUTOIMMUNE DISEASES, AND METHOD FOR TESTING FOR SAID DISEASES

TECHNICAL FIELD

The present invention relates to an analysis method for a protein involved in an autoimmune disease, and an examination method for the disease.

It should be noted that the present application claims priority from Japanese Patent Application No. 2010-256418, which is incorporated herein by reference.

BACKGROUND ART

After completion of human genome sequencing, while development of bioinformatics being promoted, analysis of genes has been made mainly based on their nucleic acid or amino acid sequences, such as search of amino acid sequences (domains) conserved across species or classification of ortholog genes based on the search. However, almost half of genes on a genome remain unknown for their functions.

In actuality, even a majority of annotated genes as well as genes quite unknown for their functions found on the genome remain unknown for their biochemical functions.

Therefore, in the post-genome era after the genome sequencing, in order to obtain more useful information on more than 25,000 kinds of genes discovered by spending a huge budget, it is essential to develop a technology for comprehensively analyzing biochemical functions of proteins (see: Non Patent Literature 1).

A method involving using a gene expression profile is known as one of such comprehensive analysis technologies as described above. Research has been made for elucidating a gene function by analyzing a gene expression profile to obtain findings to be used for development of new drugs, pharmacology, toxicology, and diagnosis. For example, statistical analysis such as correlation analysis, principal factor analysis, or analysis of variance, k average clustering, hierarchical clustering, a nearest neighbor method, discriminant analysis, a neural network, or a genetic algorithm is applied to analysis of DNA chip data (see: Patent Literatures 1 and 5 to 7).

Meanwhile, an autoimmune disease refers to a disease caused by an immune response to an antigen as a constituent of one's own body (autoantigen), i.e., autoimmunity.

When the autoantigen is present confined to a specific organ or tissue/cell, only the organ is damaged, resulting in an organ-specific autoimmune disease. As typical examples thereof, there are known myasthenia gravis and multiple sclerosis.

Meanwhile, an autoantibody against an autoantigen widely distributed throughout the body such as a nuclear substance is known to be present, and causes a systemic autoimmune disease in which a systemic lesion such as vasculitis occurs. As typical examples thereof, there are known systemic lupus erythematosus, chronic rheumatoid arthritis, and polyarteritis.

Atherosclerosis, a final presentation of a lifestyle-related disease such as hypertension, diabetes, or hyperlipidemia, causes myocardial infarction, cerebral infarction, peripheral artery disease, and the like, and thus is lethal or significantly impairs an activity of daily living (ADL) in some cases.

Therefore, early detection and prediction of development of atherosclerosis are important. Under the present circumstances, however, early-stage atherosclerosis cannot be diagnosed by conventional image diagnosis, and moreover, there is no serum marker or the like useful for the diagnosis.

Further, research outcomes in recent years have suggested a possibility that an autoimmune mechanism may be involved in part of inflammations in atherosclerosis. However, its actual mechanism remains unknown.

In recent years, it has been considered that autoimmunity is at least partially involved in the above-mentioned symptoms. However, there are still many unknown things. In contrast, in the organ-specific autoimmune disease, an etiological role of the autoantibody is clear in many cases. Based on the previous research, it has been estimated that the organ-specific autoimmune disease is caused by antigen-stimulated T lymphocytes. Various possible mechanisms have been proposed for autoantibody production. The first possible mechanism is involvement of a gene involved in production of a specific autoantibody. The second possible mechanism is that an antigen generally present in only a trace amount in blood is released in a large amount for some reasons, or an antigen is modified for some reasons. The third possible mechanism is that tolerance is broken owing to abnormality of lymphocytes involved in antibody production.

It is estimated that the autoantibody production occurs by a combination of the mechanisms (see: Patent Literature 2). Further, there are some reports on a role of the autoantibody in a systemic autoimmune disease.

JP 2009-503529 W (Patent Literature 3) discloses "Methods of detecting individuals at risk for atherosclerosis and related vascular diseases involving the detection of IL-1α autoantibodies."

However, it cannot be considered that factors involved in an autoimmune disease are only the IL-1α autoantibodies. In addition, IL-1α is excluded from the factors involved in an autoimmune disease identified by the present invention.

JP 2008-501636 W (Patent Literature 4) discloses that "the presence or absence of autoantibodies, particularly IgM autoantibodies, against phosphorylcholine is related to an increased or decreased risk of developing atherosclerosis."

However, it cannot be considered that the factors involved in an autoimmune disease are only the phosphorylcholine autoantibodies. In addition, phosphorylcholine is excluded from the factors involved in an autoimmune disease identified by the present invention.

CITATION LIST

Patent Literature

[PTL 1] JP 2008-152405 A
[PTL 2] JP 2008-118870 A
[PTL 3] JP 2009-503529 W
[PTL 4] JP 2008-501636 W
[PTL 5] JP 2008-59024 A
[PTL 6] JP 2004-30093 A
[PTL 7] JP 2005-323573 A

Non Patent Literature

[NPL 1] SEIKAGAKU, Volume 79, Issue 3, pp. 278-286, 2007

SUMMARY OF INVENTION

Technical Problem

In view of the above-mentioned present circumstances, at the present stage, it is considered that a plurality of factors, not a single factor, is involved in an autoimmune disease, and in particular, a plurality of autoantibodies against proteins are expressed.

The conventional gene expression profile (see: Patent Literatures 1 and 5 to 7) involves identifying a causative protein by comparing an expression amount of a gene in a sample derived from a patient with an autoimmune disease to an expression amount of a gene in a sample derived from a healthy subject.

However, there are many reports that an expression amount of a gene (transcription product) in samples from patients with various diseases is not necessarily consistent with an actual expression amount of a protein encoded by the gene. In addition, whether or not an autoantibody is expressed cannot be sufficiently identified by the profile.

In view of the foregoing, it is necessary to construct a detection method for a myriad of proteins involved in an autoimmune disease with high sensitivity and high efficiency and an analysis method for data resulting from the detection method.

Solution to Problem

In order to construct the above-mentioned detection method and analysis method, the inventors of the present invention have provided means for comprehensively analyzing proteins involved in an autoimmune disease by bringing a mammal-derived protein expressed in a cell-free protein synthesis system into contact with a sample derived from a patient with an autoimmune disease to detect autoantibody production, and subjecting the detected data to statistical analysis processing, and further, gene ontology analysis and/or pathway analysis.

Advantageous Effects of Invention

In the present invention, there is provided means for analyzing a protein involved in an autoimmune disease, in particular, arteriosclerosis with high sensitivity and high efficiency. There is also provided an examination method for arteriosclerosis, in particular, atherosclerosis, involving detecting an antibody titer of an autoantibody against the protein involved in arteriosclerosis obtained by the means.

That is, the present invention is as follows.

"1. An examination method for arteriosclerosis, including detecting, from a sample derived from a patient, an antibody titer of an autoantibody against any one of the following groups of proteins:

(1) a group of proteins involved in a cytokine, in which the group of proteins involved in a cytokine consists of any one or more of the following: IL-5 (interleukin-5); STX1A (Syntaxin 1A protein); CSNK2A1 (Casein Kinase II, Alpha 1 polypeptide); VAMP2 (Vesicle-associated membrane protein 2); GSK3B (Glycogen synthase kinase 3 beta); PRKCZ (Protein kinase C, zeta); PCNA (Proliferating cell nuclear antigen); PIN1 (Peptidyl-prolyl cis-trans isomerase NIMA-interacting 1); STX4 (Syntaxin-4 protein); HRB (HIV-1 Rev binding protein); HMGN1 (High Mobility Group Nucleosome Binding Domain 1); HIST1H1C (Histone Cluster 1, H1c); TUBB (Tubulin beta chain); NPM1 (Nucleophosmin also known as Nucleolar Phosphoprotein B23 or Numatrin); VAMP8 (Vesicle-Associated Membrane Protein 8); VAPA (Vesicle-associated membrane protein-associated protein A); STX3 (Syntaxin 3 protein); RABAC1 (Rab Acceptor 1 (Prenylated) protein); and CCND2 (cyclin D2 protein); and (2) a group of proteins involved in an amino acid transporter, in which the group of proteins involved in an amino acid transporter consists of any one or more of the following: SLC7A11 (protein encoded by Solute Carrier Family 7 (Anionic Amino Acid Transporter Light Chain, Xc-System), Member 11); SLC36A4 (protein encoded by solute carrier family 36 (proton/amino acid symporter), member 4); SLC7A9 (protein encoded by solute carrier family 7 (amino acid transporter light chain, bo, +system), member 9); and SLC1A3 (protein encoded by Solute Carrier Family 1 (Glial High Affinity Glutamate Transporter), Member 3).

2. An examination method according to the above-mentioned item 1, in which the group of proteins involved in a cytokine consists of any one or more of the following:
(1) IL-5;
(2) STX1A;
(3) CSNK2A1;
(4) VAMP2;
(5) GSK3B;
(6) PRKCZ;
(7) PCNA;
(8) PIN1; and
(9) STX4.

3. An examination method according to the above-mentioned item 1, in which the group of proteins involved in a cytokine consists of any one or more of the following:
(1) HRB;
(2) HMGN1;
(3) HIST1H1C;
(4) TUBB;
(5) NPM1;
(6) VAMP8;
(7) VAPA;
(8) STX3;
(9) RABAC1; and
(10) CCND2.

4. An examination method according to the above-mentioned item 1, in which the group of proteins involved in an amino acid transporter consists of any one or more of the following:
(1) SLC7A11;
(2) SLC36A4;
(3) SLC7A9; and
(4) SLC1A3.

5. An examination method according to any one of the above-mentioned items 1 to 4, in which the arteriosclerosis comprises atherosclerosis.

6. An examination method according to the above-mentioned item 5, in which the examination method is an examination of a risk of disease development, an assessment and examination of severity, or an assessment and examination of a therapeutic effect.

7. An examination kit for carrying out an arteriosclerosis examination, including at least the following: IL-5; STX1A; CSNK2A1; VAMP2; GSK3B; PRKCZ; PCNA; PIN1; STX4; HRB; HMGN1; HIST1H1C; TUBB; NPM1; VAMP8; VAPA; STX3; RABAC1; CCND2; SLC7A11; SLC36A4; SLC7A9; and/or SLC1A3.

8. An examination kit for carrying out an arteriosclerosis examination, including IL-5 and further including at least any one of the following:
(1) a microplate;
(2) a standard solution;
(3) positive and negative controls;
(4) a reaction buffer;
(5) an enzyme-labeled antibody;
(6) a washing buffer;
(7) an enzyme substrate solution; and
(8) a reaction termination solution.

9. An analysis method for a protein involved in an autoimmune disease, including the following steps of:

(1) bringing a mammal-derived protein into contact with a sample derived from a patient with an autoimmune disease to acquire autoantibody detection data (data 1);

(2) bringing the mammal-derived protein into contact with a sample derived from a healthy subject to acquire autoantibody detection data (data 2) and/or bringing the mammal-derived protein into contact with a sample derived from a patient with an autoimmune disease receiving administration of a therapeutic drug for the autoimmune disease to acquire autoantibody detection data (data 3);

(3) performing statistical analysis using any two or more of the data 1 to 3 to acquire data on one or more groups of autoantigenic proteins (mammal-derived proteins) for autoantibodies expressed differentially (data 4);

(4) annotating the groups of autoantigenic proteins of the data 4; and (5) extracting a common rule to the groups of autoantigenic proteins based on the annotation.

10. An analysis method according to the above-mentioned item 9, further including the step of performing data mining using a constraint condition based on the common rule.

11. An analysis method according to the above-mentioned item 9 or 10, further including the step of repeating the steps (1) to (5) a plurality of times using a protein having the common rule extracted in the step (5).

12. An analysis method according to any one of the above-mentioned items 9 to 11, further including the step of performing the steps (1) to (3) using a mammal-derived protein that is excluded from the data 1 to 3 and has the common rule to acquire data 5.

13. An analysis method according to any one of the above-mentioned items 9 to 12, further including the step of combining the data 5 with the data 4.

14. An analysis method according to any one of the above-mentioned items 9 to 13, in which the mammal-derived protein is expressed in a cell-free protein synthesis system.

15. An analysis method according to any one of the above-mentioned items 9 to 14, in which the step (1) and/or the step (2) include(s) detecting a mammal-derived protein that reacts with IgG using an amplified luminescent proximity homogeneous assay (ALPHA).

16. An analysis method according to any one of the above-mentioned items 9 to 15, in which the autoimmune disease includes any one selected from the following: systemic lupus erythematosus, discoid lupus erythematosus, polymyositis, scleroderma, mixed connective tissue disease, Hashimoto's thyroiditis, primary myxedema, thyrotoxicosis, pernicious anemia, Goodpasture's syndrome, rapidly progressive glomerulonephritis, myasthenia gravis, pemphigus vulgaris, bullous pemphigoid, insulin resistant diabetes, juvenile diabetes, Addison's disease, atrophic gastritis, male infertility, climacterium praecox, lens-induced uveitis, sympathetic phlebitis, multiple sclerosis, arteriosclerosis, atherosclerosis, ulcerative colitis, primary biliary liver cirrhosis, chronic active hepatitis, autoimmune hemolytic anemia, paroxysmal hemoglobinuria, sudden thrombocytopenic purpura, and Sjogren syndrome.

17. An analysis method according to any one of the above-mentioned items 9 to 16, in which the autoimmune disease includes arteriosclerosis.

18. An analysis method according to any one of the above-mentioned items 9 to 17, in which the step (4) includes gene ontology analysis.

19. An analysis method according to the above-mentioned item 18, in which the gene ontology analysis includes one or more selected from a molecular function, a cellular component, and a biological process.

20. An analysis method according to the above-mentioned item 19, in which a common rule of the gene ontology analysis includes a classified molecular function.

21. An analysis method according to the above-mentioned item 20, in which the classified molecular function is narrowed down to a lower hierarchy by repeating the steps (1) to (5).

22. An analysis method according to any one of the above-mentioned items 18 to 21, in which the autoimmune disease includes arteriosclerosis and the common rule includes an amino acid transporter.

23. An analysis method according to any one of the above-mentioned items 9 to 17, in which the step (4) includes pathway analysis.

24. An analysis method according to the above-mentioned item 23, in which the autoimmune disease includes arteriosclerosis and the common rule includes a cytokine."

BRIEF DESCRIPTION OF DRAWINGS

FIG. 1 An example of hierarchical structures of gene ontology analysis results.

FIG. 2 An example of hierarchical structures of gene ontology analysis results.

FIG. 3 Gene ontology analysis results of Example 6.

FIG. 4 Analysis results of proteins involved in an autoimmune disease by pathway analysis.

FIG. 6 Results of cluster analysis.

FIG. 7 Results of cluster analysis.

FIG. 8 Statistically processed measurement results of antibody titers of autoantibodies in patients.

FIG. 10 Gene ontology analysis results for the respective clusters.

DESCRIPTION OF EMBODIMENTS

Figure 5:
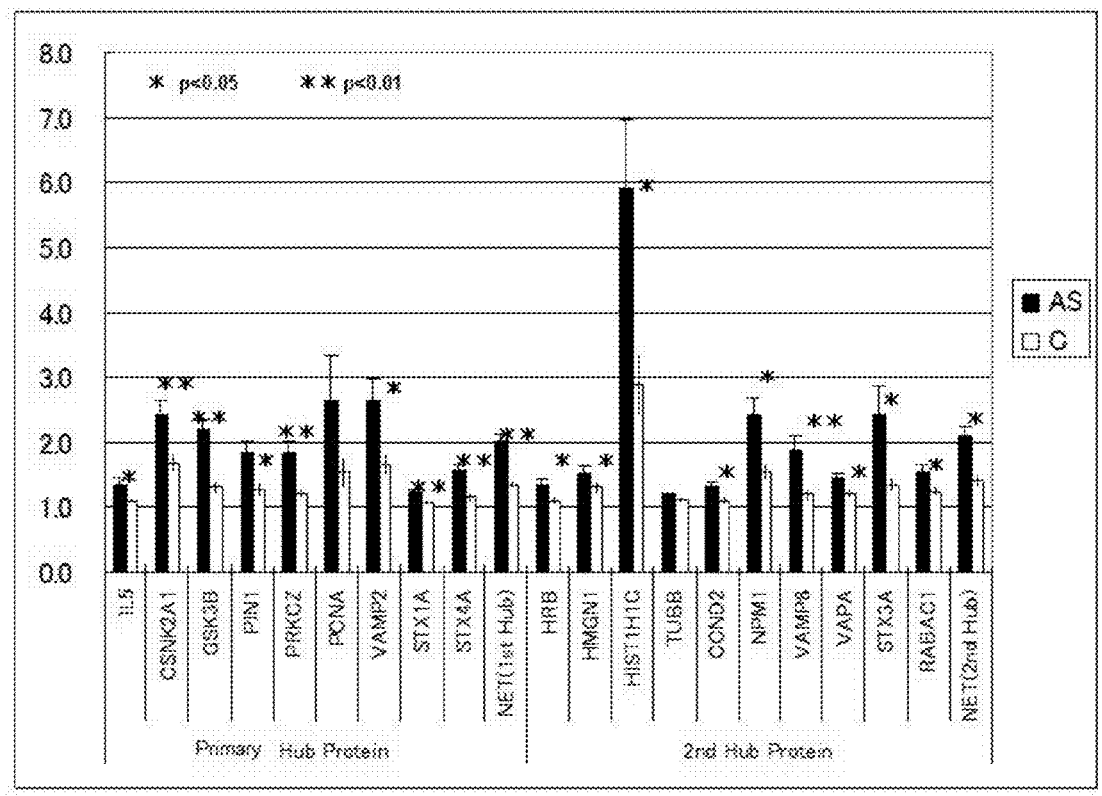
FIG. 5 Measurement results of antibody titers of autoantibodies of Example 4 (in the figure, "AS" means a serum derived from a patient with arteriosclerosis and "C" means a serum derived from a healthy subject).

Analysis Method for Protein Involved in Autoimmune Disease

An analysis method for a protein involved in an autoimmune disease of the present invention mainly has the following features.

(1) Bringing a mammal-derived protein into contact with a sample derived from a patient with an autoimmune disease to acquire autoantibody detection data (data 1).

This can identify a mammal-derived protein (autoantigenic protein) that has reacted with an autoantibody in the sample derived from the patient with an autoimmune disease.

It should be noted that the "autoantibody" is generally an IgG molecule, in particular, an IgG4 molecule, but may be an IgM, IgE, IgA, or IgD molecule.

(2) Bringing the mammal-derived protein into contact with a sample derived from a healthy subject to acquire autoantibody detection data (data 2) and/or bringing the mammal-derived protein into contact with a sample derived from a patient with an autoimmune disease receiving administration of a therapeutic drug for the autoimmune disease to acquire autoantibody detection data (data 3).

This can identify a mammal-derived protein (autoantigenic protein) that has reacted with an autoantibody in the sample derived from the healthy subject and/or in the sample derived from the patient with an autoimmune disease receiving administration of a therapeutic drug for the autoimmune disease.

(3) Performing statistical analysis using any two or more of the data 1 to 3 to acquire data on one or more groups of autoantigenic proteins (mammal-derived proteins) for autoantibodies expressed differentially (data 4).

This can identify what type of autoantibody is produced, increases, decreases, or disappears specifically in each of the healthy subject, the patient with an autoimmune disease, and the patient with an autoimmune disease receiving administration of a therapeutic drug for the autoimmune disease.

(4) Annotating the groups of autoantigenic proteins of the data 4.

This provides gene function information, disease-related information, base sequence information, public database information, homolog information with any other kind of gene, gene network information, pathway information, and the like on the autoantigenic proteins (mammal-derived proteins).

(5) Extracting a common rule to the groups of autoantigenic proteins based on the annotation.

This identifies a common rule to various autoantigenic proteins.

It should be noted that the "common rule" means that different proteins have common properties such as a timing of disease development, a molecular function, a cellular component, and a biological process.

(Autoimmune Disease)

The autoimmune disease of the present invention is any one selected from the following. In particular, the autoimmune disease is preferably arteriosclerosis, more preferably atherosclerosis.

Systemic lupus erythematosus, discoid lupus erythematosus, polymyositis, scleroderma, mixed connective tissue disease, Hashimoto's thyroiditis, primary myxedema, thyrotoxicosis, pernicious anemia, Goodpasture's syndrome, rapidly progressive glomerulonephritis, myasthenia gravis, pemphigus vulgaris, bullous pemphigoid, insulin resistant diabetes, juvenile diabetes, Addison's disease, atrophic gastritis, male infertility, climacterium praecox, lens-induced uveitis, sympathetic phlebitis, multiple sclerosis, arteriosclerosis, atherosclerosis, ulcerative colitis, primary biliary liver cirrhosis, chronic active hepatitis, autoimmune hemolytic anemia, paroxysmal hemoglobinuria, sudden thrombocytopenic purpura, and Sjogren syndrome.

(Sample)

The sample of the present invention means a biological material derived from each of a patient with an autoimmune disease under each condition (a serious condition, a mild condition, or a condition of receiving administration of a therapeutic drug for the autoimmune disease) and a healthy subject. For example, products contained in collected blood, blood-derived components (serum and plasma), urine, feces, saliva, and sweat are each used as the sample. The sample is particularly preferably a serum.

(Mammal-Derived Protein)

The mammal-derived protein of the present invention means a protein expressed in the body, in particular, blood of a mammal.

Further, the mammal of the present invention includes primates including a human (such as a gorilla, a chimpanzee, a baboon, and a squirrel monkey), companion animals (such as a cat, a rabbit, a dog, and a horse), domestic animals (such as cattle, a sheep, a pig, a goat, and a horse), and experimental animals (such as a cat, a dog, a guinea pig, a rabbit, a sheep, a goat, a pig, a chimpanzee, and a baboon).

(Contact)

The "contact" in each step of the present invention means both of adding a solution A to a solution B and adding a solution B to a solution A.

For example, when a mammal-derived protein is brought into contact with a sample derived from a patient with an autoimmune disease, a solution containing the mammal-derived protein may be added to the sample, or the sample may be added to a solution containing the mammal-derived protein.

(Data Mining)

The data mining of the present invention refers to a technology for automatically extracting regularity and causality of interest from data using a program or the like. It should be noted that the data mining to be used in the present invention includes both of a statistical technique and a non-statistical technique.

Examples of the statistical technique include principal component analysis, multiple regression analysis, factor analysis, discriminant analysis, a $\chi$-square test, Fisher's exact test, Wilcoxon's test, an F-test, a multiple test, and Welch's t-test.

Examples of the non-statistical technique include cluster analysis, a neural network, a self-organizing map, a genetic algorithm, a decision tree, a k-nearest neighbor method, and pattern recognition.

In addition, the above-mentioned techniques may be employed in combination.

(Normalization and Filtering)

In the steps of the present invention, normalization and/or filtering are/is preferably introduced.

Experiments are performed by different workers at different timings and places, and thus the degrees of backgrounds and noises vary depending on the experiments. Hence, the normalization is performed in order to make uniform the degrees of backgrounds and noises of the experiments. When protein chips are used in the steps of the present invention, image luminances (fluorescence intensities) vary depending on the chips in some cases. Accordingly, it is necessary to take a background luminance into consideration.

Further, the filtering refers to an operation involving selecting appropriate data and eliminating an error value having an adverse influence on analysis. For example, there is known a method involving setting a threshold value. Specifically, in the case of a low signal intensity (fluorescence intensity), the threshold value is set to X, and a signal intensity equal to or less than X is set to X or zero.

Further, cross-validation may be introduced.

(Gene Ontology Analysis)

In order to examine gene functions, it is necessary to classify and visualize a group of genes to be analyzed based on the gene functions. Gene ontology analysis is frequently employed as a mode of displaying the gene functions. The gene ontology was proposed by a project called Gene Ontology Consortium (http://www.geneontology.org/) established in view of the necessity of constructing a unified framework relating to gene functions. According to the gene ontology, gene functions are systematized as three pieces of information, i.e., a molecular function, a cellular component, and a biological process.

Examples of the results obtained from the gene ontology analysis are described with reference to FIG. 1 and FIG. 2.

GO IDs are identification codes of a database relating to three pieces of information, i.e., a biological process, a cellular component, and a molecular function.

Numbers in brackets on the extreme right in the ontology of FIG. 1 indicate the numbers of registered genes. At present, 32,056 genes are registered as genes having a transporter function (transport), and 1,272 genes are registered as an amino acid transporter.

In addition, in FIG. 2, the lower hierarchies of amino acid transport {e.g., acidic amino acid transport (95 genes) and amino acid transmembrane transport (8 genes)} are registered.

The gene ontology forms a structure hierarchically organized from general major classification to detailed minor classification.

(Step of Extracting Common Rule Using Gene Ontology Analysis)

The gene ontology analysis results of Example 6 below are described with reference to FIG. 3.

The four proteins shown in FIG. 3 are results obtained by the gene ontology analysis.

The group of genes of FIG. 3 is assumed to be a group of proteins found to be important in certain class separation by the statistical analysis (data mining) according to the step (3). The purpose of the step of extracting a common rule from gene annotation is to extract common properties and features from the group of genes of FIG. 3. For example, the presence or absence of an ontology commonly found in a plurality of genes is searched for the gene ontology of FIG. 3.

In FIG. 3, the "amino acid transporter" or its lower hierarchy is commonly found. This allows the possibility that there exists such a rule that a group of proteins involved in an autoimmune disease are involved in the class separation of the amino acid transporter to be found through the first steps (1) to (5).

It should be noted that in order to eliminate an experimenter bias, out of the terms of the group of proteins subjected to class separation, one having the highest frequency may be extracted as a common rule.

After the completion of the steps (1) to (5), the step of performing data mining using a constraint condition based on the extracted common rule may be added.

In the data mining, for example, with regard to the resultant data 1 to 3, data (proteins) corresponding to amino acid transporter (GO:0006865) are set as a constraint condition, and data mining, and cross-validation are performed with only a group of proteins corresponding to the condition. Thus, to what degree the amino acid transporter contributes to the class separation can be quantitatively grasped.

Further, the upper hierarchy of amino acid transporter (GO:0006865) is amine transport (GO:0015837). Thus, in another data mining, with regard to the resultant data 1 to 3, data (proteins) corresponding to amine transport (GO:0015837) are set as a constraint condition, and data mining and cross-validation are performed with only a group of proteins corresponding to the condition. Thus, to what degree the amine transporter contributes to the class separation can be quantitatively grasped.

In addition, the lower hierarchy of amino acid transporter (GO:0006865) is acidic amino acid transport (GO:0015800). Thus, in another data mining, with regard to the resultant data 1 to 3, data (proteins) corresponding to acidic amino acid transport (GO:0015800) are set as a constraint condition, and data mining and cross-validation are performed with only a group of proteins corresponding to the condition. Thus, to what degree the acidic amino acid transporter contributes to the class separation can be quantitatively grasped.

If the result (accuracy rate or error rate) obtained in the case of performing data mining using "including acidic amino acid transport" as a constraint condition is compared to the result obtained in the case of performing data mining using a constraint condition including "amine transport" and the result obtained in the case of performing data mining using a constraint condition including "amino acid transport," when the result obtained in the case of performing data mining using "including acidic amino acid transport" as a constraint condition is better than the latter two results, it is found that "acidic amino acid transport," rather than "amino acid transporter" and "amine transporter", is important for the class separation. This allows the molecular function of a protein involved in an autoimmune disease to be narrowed down from the upper hierarchy to the lower hierarchy.

That is, a common rule having higher generality can be extracted by repeating the above-mentioned steps a plurality of times.

In addition, data 5 can be acquired as additional data by carrying out the steps (1) to (3) using a protein that is excluded from the data 1 to 3 and has a common rule characteristic. Moreover, a common rule having high accuracy and higher generality can be extracted by combining the data 5 with the data 4.

Pathway analysis is described with reference to FIG. 4 obtained from this example. In FIG. 4, circles indicate genes, and lines connecting the circles indicate that there is an interrelationship. It should be noted that an interrelationship score is omitted in FIG. 4. In general, the interrelationship score refers to the number of cases where two genes connected with a line exist in the same abstract of the medical literature database MEDLINE.

Further, nine kinds of proteins (IL-5, STX1A, CSNK2A1, VAMP2, GSK3B, PRKCZ, PCNA, PIN1, and STX4) can each be identified as one hub protein. In addition, ten kinds of proteins (HRB, HMGN1, HIST1H1C, TUBB, NPM1, VAMP8, VAPA, STX3, RABAC1, and CCND2) can each be identified as another hub protein.

As a literature database, MEDLINE or OMIM of NCBI, U.S. is generally used, but any other literature database may be used.

(Step of Extracting Common Rule Using Pathway Analysis)

The step of extracting a common rule to proteins involved in an autoimmune disease by pathway analysis is described. Further, known software {e.g.: Pathway Assist ver 3.0 (Ariadne Genomics)} may be used as pathway analysis software.

As described above, a list of expressed proteins including the data 4 on one or more groups of proteins (autoantigenic proteins) expressed differentially is prepared.

Then, the prepared list of expressed proteins is imported to the pathway analysis software. It should be noted that in Examples below, pathway analysis was performed using known pathway analysis software according to the protocol of the instruction manual attached thereto.

Next, a pathway in the list of expressed proteins is calculated. That is, an association between molecules linked by the processing algorithm (Natural Language Processing Engine) of the pathway analysis software is searched from among abstracts of articles that can be searched in the MEDLINE database, which is a public database that stores biomedical literature information.

Then, when the association between molecules is extracted, a pathway showing the association between molecules is calculated.

When the association between molecules linked by the algorithm of the pathway analysis software from among abstracts of articles that can be searched in the MEDLINE database is extracted, a node is displayed on a pathway drawing screen.

Next, a common rule to a group of hub proteins (in FIG. 4: IL-5, STX1A, CSNK2A1, VAMP2, GSK3B, PRKCZ, PCNA, PIN1, and STX4) is extracted. For example, in this example, the following rule can be extracted: part of each group of proteins is a protein related with a cytokine (human cytokine) in a statistically significant manner (common rule). It should be noted that the gene ontology analysis described above may be utilized for extracting the common rule.

Further, with regard to a correlation between the group of proteins identified by the pathway analysis and an autoimmune disease, the correlation between the group of proteins identified by the pathway analysis and the autoimmune disease can be verified by confirming a correlation with expression levels of the group of proteins in the data 1 to 3.

Accordingly, the prediction that it is highly probable that there is a correlation between the identified group of proteins and the autoimmune disease can be ensured more by performing verification a plurality of times.

In addition, the data mining step and other steps may be added as described in paragraphs "0026" and "0027."

(Cell-Free Protein Synthesis System)

The mammal-derived protein to be used in the present invention is expressed through use of preferably a cell-free protein synthesis system, more preferably an extract for cell-free protein synthesis using wheat germ or the like derived from a eukaryote.

As a commercially available extract for protein synthesis, there are given, for example, Rabbit Reticulocyte Lysate System (Promega KK) derived from rabbit reticulocytes and Wheat Germ Expression Premium Kit (WEPRO™, CellFree Sciences Co., Ltd.) derived from wheat germ.

The best extract to be applied to the present invention is an extract derived from wheat germ, the extract being substantially free of an endosperm constituent or a metabolite such as glucose, which causes protein synthesis inhibition, in a germ tissue cell as contaminants. It should be noted that the extract substantially free of an endosperm constituent means that the deadenylation ratio of a ribosome is 7% or less, preferably 1% or less. In addition, it is suitable that the concentrations of a sugar and a phosphorylated sugar in the cell extract are reduced to 10 mM or less, preferably 6 mM or less (in terms of glucose concentration in an extract having an absorbance at 260 nm of 200 OD/ml). A preparation method for such extract is exemplified in WO 2005/063979 A1.

It should be noted that one of the features of the present invention is, for example, as follows: it is not necessary to wash a biotinylated mammal-derived protein after synthesis as shown in Example 3 below by expressing a mammal-derived protein in a wheat germ cell-free protein synthesis system. That is, it is not necessary to remove biotin unbound to a sequence for biotinylation.

This allows the antibody titer of an autoantibody against a mammal-derived protein in a large number to be efficiently measured in the analysis method of the present invention.

(Acquisition of Autoantibody Detection Data)

The "acquisition of autoantibody detection data" of the present invention means detecting an autoantibody specifically expressed in a patient with an autoimmune disease, and more specifically means measuring the antibody titer of the autoantibody. It should be noted that a method known per se may be utilized as a detection method for the antibody titer.

In the present invention, the data can be acquired by inputting numerical values for the antibody titers of one or more detected autoantibodies to an Excel file (manufactured by Microsoft) or the like.

(Detection System for Antibody Titer of Autoantibody)

In the present invention, a detection method for the antibody titer of an autoantibody is not particularly limited. However, a homogeneous assay, which allows a washing step to be omitted, in particular, ALPHA is preferably used as a detection system.

In the present invention, a protein expressed in a large number can be detected efficiently and with high accuracy through use of preferably ALPHA.

{Amplified Luminescent Proximity Homogeneous Assay) (ALPHA)}

ALPHASCREEN™ (i.e., Amplified Luminescent Proximity Homogeneous Assay Screen, an assay protocol for measuring analytes using a homogenous protocol) (PerkinElmer) is a typical assay method for the ALPHA.

The method is an analysis method based on the transfer of singlet oxygen between donor beads and acceptor beads brought into proximity with each other. In this method, in excitation at 680 nm, a photosensitizer in the donor beads converts oxygen at the surroundings into oxygen in a singlet state, and the oxygen diffuses 29 to a distance of 200 nm. A chemiluminescent group in the acceptor beads transfers energy to a fluorescence acceptor in the beads, and subsequently emits light at about 600 nm. It should be noted that the acceptor beads are each an inactive carrier made of glass, a silica gel, a resin, or the like, the carrier being used for immobilizing the above-mentioned biomolecule. The donor beads are each an inactive carrier made of glass, a silica gel, a resin, or the like, the carrier being used for immobilizing streptavidin.

(In Vitro Detection of Autoantibody Titer Using ALPHA)

A mammal-derived protein which has been subjected to biotinylation (sometimes referred to as biotinylated mammal-derived protein), acceptor beads {Anti-IgG (protein G) Acceptor Beads} capable of directly or indirectly recognizing the biotinylated substrate, streptavidin-bound donor beads, and a sample (serum) derived from a patient with an autoimmune disease and/or a sample derived from a healthy subject are added to a microplate.

In this case, when an autoantibody against the biotinylated mammal-derived protein is expressed, the autoantibody recognizes (binds to) the biotinylated mammal-derived protein as an antigen. Thus, the donor beads and the acceptor beads come into proximity with each other. As a result, a rise in signal occurs.

On the other hand, when an autoantibody against the biotinylated mammal-derived protein is not expressed, the autoantibody does not recognize (bind to) the biotinylated mammal-derived protein as an antigen. Thus, the donor beads and the acceptor beads cannot come into proximity with each other. As a result, no rise in signal occurs.

It should be noted that a detection method for the signal involves, for example, measurement using the intensity of fluorescence emitted from the acceptor beads.

(Detection of Autoantibody Titer Using Immunoassay)

In the present invention, the antibody titer of an autoantibody can be detected by bringing a mammal-derived protein or a fragment thereof into contact with a sample (in particular, a serum) derived from a patient with an autoimmune disease, in particular, arteriosclerosis. An autoantibody that binds to the mammal-derived protein or fragment thereof can be detected by an immunoassay known per se. A specific method therefor is as described below, but is not particularly limited thereto.

(Non-Competitive Immunoassay)

An autoantibody that binds to a mammal-derived protein or a fragment thereof is detected with an anti-human immunoglobulin antibody. At this time, when the mammal-derived protein or fragment thereof or the anti-human immunoglobulin antibody is immobilized to a solid phase in advance, the removal of unreacted components (generally called B/F separation) can be easily performed by washing.

For example, after the mammal-derived protein or fragment thereof immobilized to a solid phase has been brought into contact with a patient serum, the serum is removed and the anti-human immunoglobulin antibody is then added. When the anti-human immunoglobulin antibody is labeled in advance, the amount of the label bound to the solid-phase increases in proportion to the amount of an autoantibody. The anti-human immunoglobulin antibody corresponds to an antibody called a secondary antibody. When an antibody capable of distinguishing an antibody class is utilized as the anti-human immunoglobulin antibody, the autoantibody can be detected for each class. The mammal-derived protein or fragment thereof, the sample (e.g.: serum), and the anti-human immunoglobulin antibody may be simultaneously subjected to a reaction.

A particle agglutination reaction or immunochromatography may be utilized as the non-competitive immunoassay. The particle agglutination reaction is a detection method based on such a phenomenon that an autoantibody causes the agglutination of particles sensitized with a mammal-derived protein or a fragment thereof.

On the other hand, the immunochromatography is designed so that the above-mentioned mammal-derived protein or fragment thereof immobilized to a solid phase, which is present in a chromatograph medium, is subjected to a reaction with an autoantibody in a sample and then with a labeled anti-human immunoglobulin antibody, and in parallel with the reaction, the separation of unreacted components in the chromatograph medium is performed.

(Competitive Immunoassay)

An autoantibody can be detected through utilization of such a phenomenon that the autoantibody inhibits an immunological reaction between a mammal-derived protein or a fragment thereof and an antibody against the mammal-derived protein or fragment thereof. Also in this case, the removal of unreacted components can be simply performed through utilization of a solid phase. That is, when the mammal-derived protein or fragment thereof is brought into contact with the antibody against the mammal-derived protein or fragment thereof in the presence of a blood sample, any one of the antibody against the mammal-derived protein or fragment thereof and the mammal-derived protein or fragment thereof is immobilized to a solid phase, and the other is labeled to be used. In addition, after B/F separation, the autoantibody can be detected based on the amount of the label bound to the solid-phase. In the case of performing the competitive immunoassay, the antibody against the mammal-derived protein or fragment thereof to be used as a reaction component may be a polyclonal antibody or a monoclonal antibody as long as it competes with the autoantibody.

(Suppressive Immunoassay)

A mammal-derived protein or a fragment thereof is brought into contact with a sample, and then subjected to a reaction with an antibody against the mammal-derived protein or fragment thereof. When an autoantibody against the mammal-derived protein or fragment thereof is absent in the sample, a reaction between the mammal-derived protein or fragment thereof and the antibody against the mammal-derived protein or fragment thereof is not inhibited. On the other hand, when the autoantibody against the mammal-derived protein or fragment thereof is present in the sample, the inhibition occurs.

Specifically, first, a mammal-derived protein or fragment thereof immobilized to a solid phase is added to a sample, and sufficiently subjected to a reaction with the sample. After that, an antibody against the mammal-derived protein or fragment thereof is further added. When the antibody against the mammal-derived protein or fragment thereof is labeled in advance, the presence of an autoantibody can be confirmed by measuring the amount of the label bound (or unbound) to the solid phase. Alternatively, a labeled mammal-derived protein or fragment thereof may be brought into contact with a sample, and brought into contact with an antibody against the mammal-derived protein or fragment thereof immobilized to a solid phase. This method has an advantage particularly when applied to immunochromatography.

As a label to be used for an immunoassay, there are known, for example, a fluorescent substance, a luminescent substance, a pigment, an enzyme, a coenzyme, and a radioisotope. Of those, enzyme labels such as alkaline phosphatase and peroxidase are advantageous label components because they are excellent in safety and economic efficiency and can achieve required sensitivity in a relatively easy manner.

A reaction component such as the anti-human immunoglobulin antibody or the mammal-derived protein or fragment thereof may be directly labeled with any such label component, or may be indirectly labeled through utilization of, for example, an antibody that recognizes any such component, or an avidin-biotin system. In order to achieve the binding of various antibodies to a solid-phase, through use of a solid-phase carrier such as a microplate, plastic beads, or synthetic resin fine particles, physical adsorption, chemical binding, or an indirect binding method involving using avidin-biotin is generally utilized. A carrier in which any such immune component is immobilized to a solid phase can be treated with an inactive protein such as bovine serum albumin or skim milk to suppress a non-specific reaction. It should be noted that when the solid phase and the enzymatic label are used in combination, the immunoassay is particularly called ELISA.

Examples of the detection method for the autoantibody titer except the foregoing include, but not particularly limited to, an indirect fluorescent antibody method, an turbidimetric immunoassay, a nephelometric immunoassay, a double immunodiffusion method (DID method), a latex agglutination method, and a chemiluminescence method (e.g., a chemiluminescence enzyme immunoassay).

(Examination Method)

The examination for an autoimmune disease, in particular, arteriosclerosis of the present invention involves detecting, from a sample, in particular, a serum derived from a patient, an antibody against any one or more of the following groups of proteins.

It should be noted that the examination of the present invention includes an examination of a risk of disease development, an assessment and examination of severity, and an assessment and examination of a therapeutic effect.
(1) Group of proteins involved in a cytokine
(2) Group of proteins involved in an amino acid transporter The group of proteins involved in a cytokine preferably includes, but not particularly limited to, interleukin-5 (IL-5), syntaxin 1A (STX1A), casein kinase 2, alpha 1 polypeptide (CSNK2A1), vesicle-associated membrane protein 2 (synaptobrevin 2) (VAMP2), glycogen synthase kinase 3 beta (GSK3B), protein kinase C, zeta (PRKCZ), proliferating cell nuclear antigen (PCNA), syntaxin 4 (STX4), and peptidyl-prolyl cis/trans isomerase, NIMA-interacting 1 (PIN1), and/or HIV-1 Rev binding protein (HRB), high-mobility group nucleosome binding domain 1 (HMGN1), histone cluster 1, H1c (HIST1H1C), tubulin, beta (TUBB), nucleophosmin (nucleolar phosphoprotein B23, numatrin) (NPM1), vesicle-associated membrane protein 8 (VAMP8), vesicle-associated membrane protein (VAMP)-associated protein A (VAPA), SYNTAXIN 3 (STX3), cyclin D2 (CCND2), and Rab acceptor 1 (RABAC1).

Examples of the group of proteins involved in an amino acid transporter preferably includes, but not particularly limited to, solute carrier family 7, (cationic amino acid transporter, y+ system) member 11 (SLC7A11), solute carrier family 36 (proton/amino acid symporter), member 4 (SLC36A4), solute carrier family 7 (cationic amino acid transporter, y+ system), member 9 (SLC7A9), and solute carrier family 1 (glial high affinity glutamate transporter), member 3 (SLC1A3).

In addition, of the protein groups, IL-5 is preferred from the results of Examples 9 to 11 described below. Further, IL-5 includes not only full length (SEQ ID NO:1) but also partial sequences ((e.g., IL-5 (20-135 which means position 20 to position 135 of IL-5 (SEQ ID NO:2). Hereinafter it has the same meaning), IL-5 (64-135 which means position 64 to position 135 of IL-5 (SEQ ID NO:3). Hereinafter it has the same meaning)), particularly secretory IL-5 (IL-5 (20-135) (SEQ ID NO:2)).

(Examination Kit)
The examination kit for an autoimmune disease, in particular, arteriosclerosis according to the present invention can be a kit for carrying out the above-mentioned ELISA, chemiluminescence method, immunochromatography, or the like. In particular, the ELISA kit includes IL-5, STX1A, CSNK2A1, VAMP2, GSK3B, PRKCZ, PCNA, PIN1, STX4, HRB, HMGN1, HIST1H1C, TUBB, NPM1, VAMP8, VAPA, STX3, RABAC1, CCND2, RABAC1, SLC7A11, SLC36A4, SLC7A9, and/or SLC1A3, and further includes any one of the following components:
(1) a microplate;
(2) a standard solution;
(3) a positive and negative controls;
(4) a reaction buffer;
(5) an enzyme-labeled antibody;
(6) a washing buffer;
(7) an enzyme substrate solution; and
(8) a reaction termination solution.

The present invention is described in detail below with reference to examples, but the scope of the present invention is not limited to these examples.

Example 1

Preparation of Sample Derived from Patient with Autoimmune Disease

In this example, sera obtained from patients with atherosclerosis (23 patients) were used as samples. In addition, the samples were divided into ones from mild patients, serious patients, mild and old patients, and serious and old patients to be analyzed.

It should be noted that sera derived from healthy subjects were each used as a control.

Example 2

Preparation of Translation Template Encoding Biotinylated Mammal-Derived Protein mRNA as a translation template was prepared as described below. Vectors as biotinylated protein transcription templates obtained by fusing a biotin tag to genes encoding various mammal-derived proteins (about 3,000 kinds) were prepared (pEU-biotinylated tag-various mammal-derived proteins). Based on each of the vectors, a PCR product including the Q sequence portion of a tobacco mosaic virus (TMV) was used as a template. The transcription template was added to a transcription reaction solution (final concentration: mM HEPES-KOH, pH 7.8, 16 mM magnesium acetate, 10 mM dithiothreitol, 2 mM spermidine, 2.5 mM 4NTPs (4 kinds of nucleotide triphosphates), 0.8 U/µL RNase inhibitor, 1.6 U/µL SP6 RNA polymerase), and the mixture was subjected to a reaction at 37° C. for 3 hours. The resultant RNA was extracted with phenol/chloroform, precipitated with ethanol, and then purified with Nick Column (manufactured by Amersham Pharmacia Biotech) to prepare a translation template.

Example 3

Translation Reaction Step of Biotinylated Mammal-Derived Protein

A 96-well titer plate was used as a reaction vessel.
First, 125.0 µL of a feed phase (62.5 µL of 2× Substrate Mixture, 1.25 µL of 50 µM biotin, 61.25 µL of MilliQ) were added to the titer plate. Next, a mixture obtained by adding each translation template {pelleted translation template (mRNA) dissolved with 25 µL of a reaction solution} of Example 2 above to 25.0 µL of a reaction phase (0.25 µL of 4 µg/µL creatine kinase, 6.5 µL of a wheat germ extract for cell-free protein synthesis (200 O.D.), 1.0 µL of a biotinylation enzyme (180 O.D.), 8.75 µL of 2× Substrate Mixture, 2.5 µL of 5 µM biotin, 3.5 µL of MilliQ) was added carefully and gently to the bottom of the titer plate. The resultant was left to stand still at 26° C. for 15 to 20 hours to perform a protein synthesis reaction.

The biotinylated protein after the completion of synthesis was used in the following examples without purification.

Example 4

Measurement of Antibody Titer of Autoantibody Using Alpha Screen™

A 384-well titer plate (Optiplate-384TPP) was used as a reaction vessel.
8.0 µL of Mixture A {6.0 µL of MillQ, 1.0 µL of 10× AlphaScreen Buffer (1 M Tris-HCl, pH 8.0/0.1% Tween20), 1.0 µL of 10 mg/mL BSA}, 10 µL of a serum {(+): 2.5×10$^{-3}$ dilution}, and 5.0 µL of each of various biotinylated mammal-derived proteins (5-fold dilution, using Biomek FX) in Example 3 above were added to each of the wells, and left to stand still at 26° C. for 30 minutes.

After the leaving to stand still, 10 µL of Mixture B (7.88 µL of MillQ, 1.0 µL of 10× AlphaScreen Buffer (1 M Tris-HCl, pH 8.0/0.1% Tween20), 1.0 μL of 10 mG/mL BSA, 0.06 μL of {5 mG/mL StreptAvidin Donor Beads, 0.06 μL of 5 mG/mL Anti-IgG (protein G) Acceptor Beads} were further added to each of the wells and left to stand still at 26° C. for 60 minutes.

After the leaving to stand still, a fluorescence intensity (autoantibody titer) was measured using EnVision.

FIG. 5 shows part of the results of the autoantibodies in the above-mentioned measurement.

The above-mentioned results revealed that different mammal-derived proteins provided different autoantibody detection results.

In addition, data on an autoantigenic protein having a high antibody titer was acquired.

Example 5

Analysis of Autoantigenic Protein Specifically Expressed in Autoimmune Disease

Data on the fluorescence intensity (autoantibody titer) of a sample derived from each of the patients {mild patients, serious patients, mild and old patients, and serious and old patients} obtained in Example 4 above was compared to data on the fluorescence intensity (autoantibody titer) of a sample derived from a healthy subject as a control, to thereby acquire data on a group of autoantigenic proteins for autoantibodies expressed differentially (in particular, autoantibodies with increased expression).

More specifically, the respective data were subjected to natural logarithmic transformation, and then converted into scores using a mean and a standard deviation (when an mean value, +1SD, and +2SD were defined as 0, 1, and 2, respectively). In addition, 382 kinds of proteins with the highest scores were selected.

(2) Through use of cluster analysis (a correlation heatmap was prepared using heatmap2 of statistical software R (http://www.r-project/org)), a group of the 382 kinds of proteins was divided into four groups, which were groups of proteins highly associated with each other.

It should be noted that clusters 1 to 4 were groups consisting of 126 proteins (see: FIGS. 6 and 7), 62 proteins (see: FIGS. 6 and 7), 129 proteins (see: FIGS. 6 and 7), and 65 proteins (see: FIGS. 6 and 7), respectively.

FIG. 8 shows part of data of the above-mentioned analysis results. It should be noted that Ha1, Ha2, Ha3, and Ha4 indicate a mild patient, a serious patient, a mild and old patient, and a serious and old patient, respectively.

As apparent from the results of FIG. 8, it was found that the antibody titers of the autoantibodies varied depending on the disease conditions.

Figure 9:
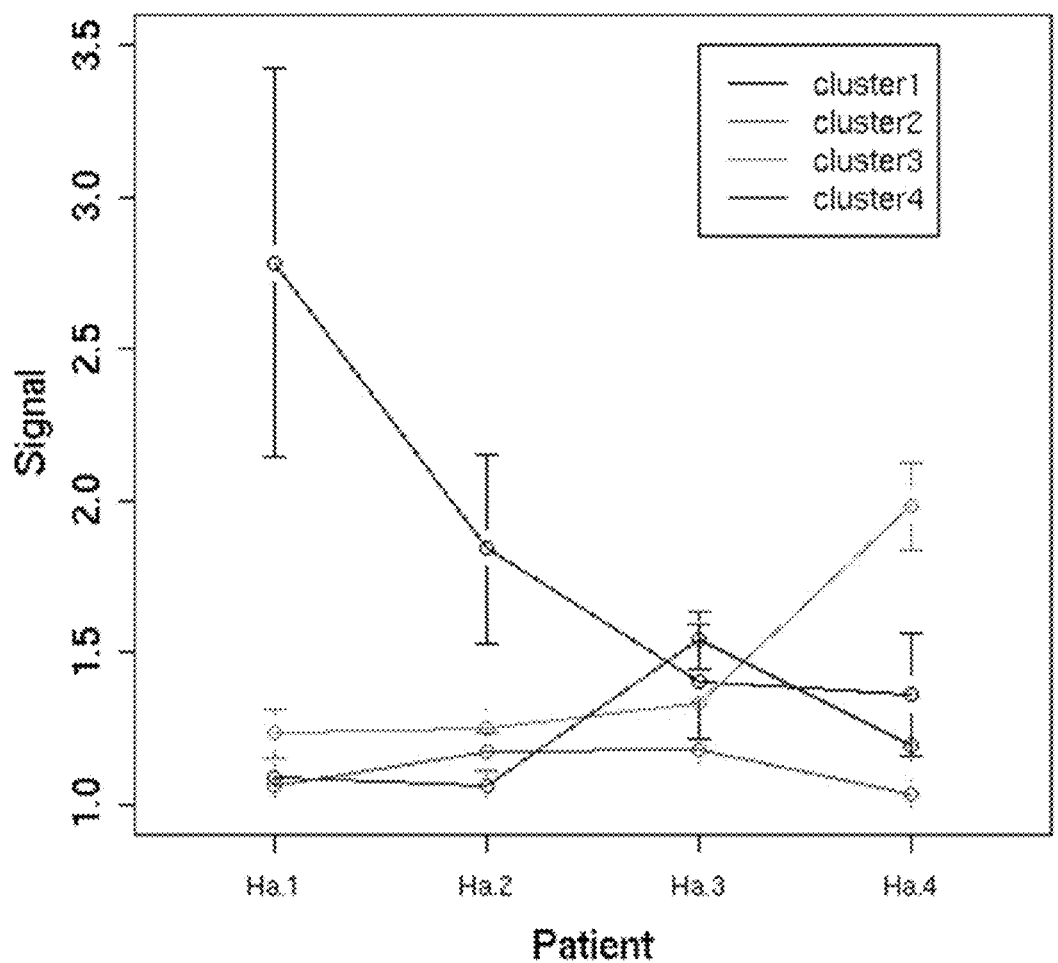
FIG. 9 Average profiles for respective clusters in patients.

Further, FIG. 9 shows average profiles for the respective clusters in the patients.

As apparent from the results of FIG. 9, it is found that the antibody titers of the autoantibodies vary depending on the disease conditions and the clusters.

In particular, the antibody titers of the autoantibodies against the proteins belonging to cluster 1 were found to be very high.

As apparent from the analysis results shown in FIG. 8 and FIG. 9, it was found that in the patients with an autoimmune disease, in particular, arteriosclerosis, the amounts and kinds of the autoantibodies expressed in sera varied depending on progression of the disease, age, and the like.

This allows a risk of development and severity of, and a therapeutic effect on, an autoimmune disease, in particular, arteriosclerosis to be assessed by detecting an autoantigenic protein against an autoantibody in a serum.

Example 6

Analysis of Protein Involved in Autoimmune Disease by Gene Ontology Analysis

The data for each cluster on the group of proteins expressed differentially in an autoimmune disease, in particular, atherosclerosis acquired in Example 5 above was imported to a public database (http://www.geneontology.org/).

FIG. 10 shows part of the imported results.

As shown in FIG. 10, it is found that the clusters have terms different from each other. It should be noted that the calculated values (Pvalue) of FIG. 10 are calculation results obtained by comparing a plurality of groups of signal values with each other and performing a test. The terms indicate gene functions.

In addition, frequently appearing terms are as follows: amino acid transporter for cluster 1; inflammation, carbohydrate metabolism, and steroid metabolism for cluster 2; translation, transcription, and recombination for cluster 3; and RNA catabolism for cluster 4.

The proteins each belonging to cluster 1 and having a term "amino acid transporter" or a lower hierarchy concept of "amino acid transporter" were extracted and shown in FIG. 3.

This allows SLC7A11, SLC36A4, SLC7A9, and SLC1A3 as the group of proteins shown in FIG. 3 to be assessed to be proteins involved in an autoimmune disease, in particular, arteriosclerosis.

That is, a risk of development and severity of, and a therapeutic effect on, an autoimmune disease, in particular, arteriosclerosis, in more particular, atherosclerosis can be assessed by detecting and measuring the antibody titers of autoantibodies against SLC7A11, SLC36A4, SLC7A9, and SLC1A3 in a sample, in particular, a serum derived from a patient with an autoimmune disease, in particular, atherosclerosis.

Example 7

Analysis of Protein Involved in Autoimmune Disease by Pathway Analysis

The data on the group of proteins expressed differentially in an autoimmune disease, in particular, atherosclerosis acquired in Example 5 above was analyzed with known software {GeneSphere, Fujitsu (http://venus.netlabor atory.com/drug_discovery/genesphere/feature/)}. A pathway showing a significant variation in expression in the group of patients with an autoimmune disease as compared to the group of healthy subjects when protein expression was evaluated for each pathway was extracted.

FIG. 4 illustrates the results of the analysis.

From the results of FIG. 4, there were identified 14 kinds of proteins (IL-5, STX1A, CSNK2A1, VAMP2, GSK3B, PRKCZ, PCNA, PIN1, STX4, HRB, HMGN1, HIST1H1C, TUBB, NPM1, VAMP8, VAPA, STX3, RABAC1, and CCND2).

This allows IL-5, STX1A, CSNK2A1, VAMP2, GSK3B, PRKCZ, PCNA, PIN1, and STX4, and further, HRB, HMGN1, HIST1H1C, TUBB, NPM1, VAMP8, VAPA, STX3, RABAC1, and CCND2 as the group of proteins shown in FIG. 4 to be assessed to be proteins involved in an autoimmune disease, in particular, arteriosclerosis, in more particular, atherosclerosis.

That is, a risk of development and severity of, and a therapeutic effect on, an autoimmune disease, in particular, atherosclerosis can be assessed by detecting and measuring the antibody titers of autoantibodies against IL-5, STX1A, CSNK2A1, VAMP2, GSK3B, PRKCZ, PCNA, PIN1, and STX4, and further, HRB, HMGN1, HIST1H1C, TUBB, NPM1, VAMP8, VAPA, STX3, RABAC1, and CCND2 in a sample, in particular, a serum derived from a patient with an autoimmune disease, in particular, arteriosclerosis, in more particular, atherosclerosis.

Example 8

Confirmation with Each Protein Obtained by Analysis in Examples Above

Through use of each of the proteins obtained by the analysis described above (IL-5, STX1A, CSNK2A1, VAMP2, GSK3B, PRKCZ, PCNA, PIN1, STX4, HRB, HMGN1, HIST1H1C, TUBB, NPM1, VAMP8, VAPA, STX3, RABAC1, CCND2, SLC7A11, SLC36A4, SLC7A9, and SLC1A3), the antibody titer of an autoantibody in a serum derived from a patient was measured by the same method as in Example 4.

The majority of the above-mentioned proteins showed a significantly high antibody titer as compared to the control, i.e., the sample derived from the healthy subject.

This allows a risk of development and severity of, and a therapeutic effect on, an autoimmune disease, in particular, atherosclerosis to be assessed using each of the proteins obtained by the analysis described above.

In addition, the analysis method of the present invention was found to be excellent as an analysis method for a protein involved in an autoimmune disease.

Example 9

Measurement of Antibody Titer of Anti-IL-5 Antibody

The antibody titer of the anti-IL-5 antibody, which served as an indicator for the assessment of a risk of development and severity of, and a therapeutic effect on, an autoimmune disease, in particular, atherosclerosis, was measured in detail by Examples 1 to 8 above. The details thereof are as described below.

By the same method as in Examples 2 to 4 above, based on genes encoding full length IL-5 (SEQ ID NO:1), and secretory IL-5 (20-135) (SEQ ID NO:2) and partial sequence IL-5 (64-135) (SEQ ID NO:3) each having a higher antibody titer than that of full length IL-5 (SEQ ID NO:1), biotinylated full length IL-5, biotinylated IL-5 (20-135), and biotinylated IL-5 (64-135) were expressed with a wheat germ extract for cell-free protein synthesis.

In addition, each of biotinylated full length IL-5, biotinylated secretory IL-5 (20-135), and biotinylated partial sequence IL-5 (64-135) was added to sera derived from patients with ischemic heart disease (IHD) and patients with arteriosclerosis obliterans (ASO) to measure the antibody titers of the anti-IL-5 antibody.

Figure 11:
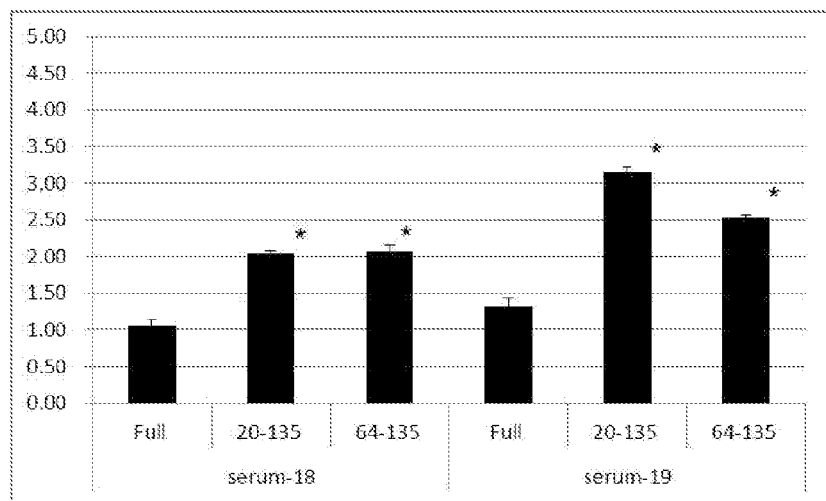
FIG. 11 Measurement results of antibody titers of an anti-IL-5 antibody in sera from patients with ischemic heart disease with addition of various types of IL-5.

FIG. 11 shows the measurement results of the antibody titers of the anti-IL-5 antibody in the sera from the patients with ischemic heart disease when full length IL-5 (SEQ ID NO:1), secretory IL-5 (20-135) (SEQ ID NO:2), and partial sequence IL-5 (64-135) (SEQ ID NO:3) were added to the sera from the patients with ischemic heart disease.

As shown in FIG. 11, it was confirmed that the anti-IL-5 antibody in the sera from the patients with ischemic heart disease recognized secretory IL-5 (20-135) (SEQ ID NO:2) and partial sequence IL-5 (64-135) (SEQ ID NO:3) more strongly than full length IL-5 (SEQ ID NO:1).

Figure 12:
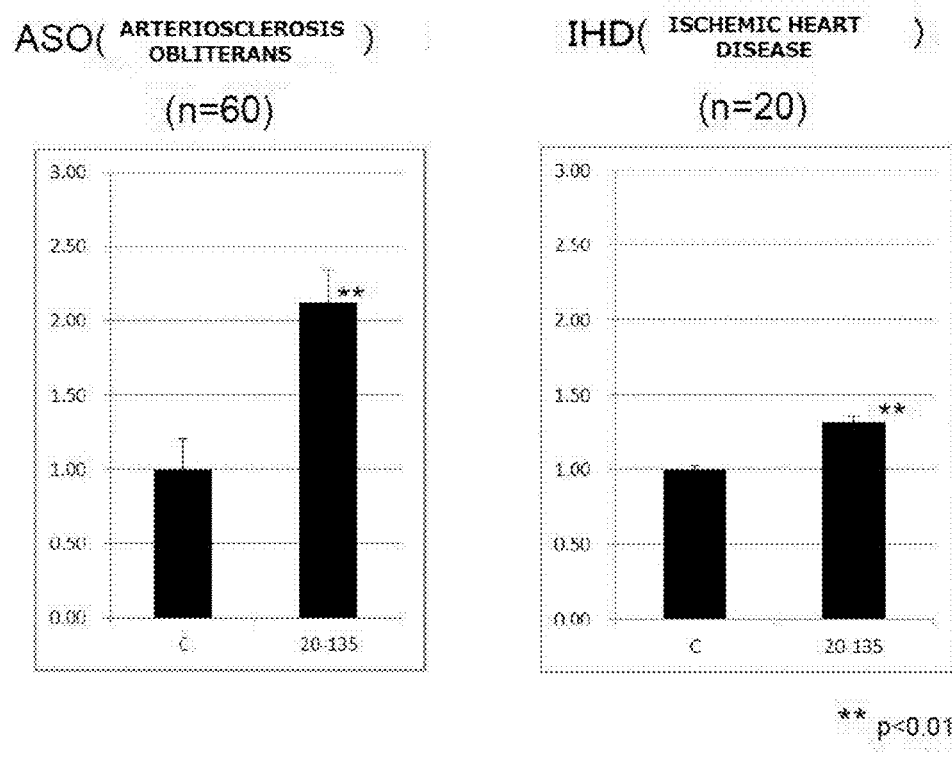
FIG. 12 Measurement results of antibody titers of the anti-IL-5 antibody in sera from patients with arteriosclerosis obliterans and patients with ischemic heart disease with addition of secretory IL-5 (20-135) (in the figure, "C" indicates no addition of secretory IL-5 (20-135)).

FIG. 12 shows the measurement results of the antibody titers of the anti-IL-5 antibody in the sera from the patients with arteriosclerosis obliterans and the patients with ischemic heart disease with addition of secretory IL-5 (20-135) (SEQ ID NO:2).

As shown in FIG. 12, it was confirmed that the anti-IL-5 antibody in the sera from the patients with arteriosclerosis obliterans and the patients with ischemic heart disease recognized secretory IL-5 (20-135) (SEQ ID NO:2).

Thus, the anti-IL-5 antibody in the sera from the patients with arteriosclerosis obliterans and the patients with ischemic heart disease recognizes not only full length IL-5 (SEQ ID NO:1) but also secretory IL-5 (20-135) (SEQ ID NO:2) and partial sequence IL-5 (64-135) (SEQ ID NO:3). This allows an autoimmune disease, in particular, arteriosclerosis to be inspected by detecting an autoantibody against secretory IL-5 (20-135) (SEQ ID NO:2) and partial sequence IL-5 (64-135) (SEQ ID NO:3) from a serum from a patient.

Example 10

Measurement of Concentration of IL-5 in Serum from Patient with Arteriosclerosis The concentrations of IL-5 in sera from patients with ischemic heart disease as patients with arteriosclerosis (n=20) and in sera derived from healthy subjects (n=10) were measured by ELISA (IMMUNOTECH, Mareille, France).

It should be noted that IL-5 was expressed with a wheat germ extract for cell-free protein synthesis based on an IL-5 gene sequence.

Figure 13:
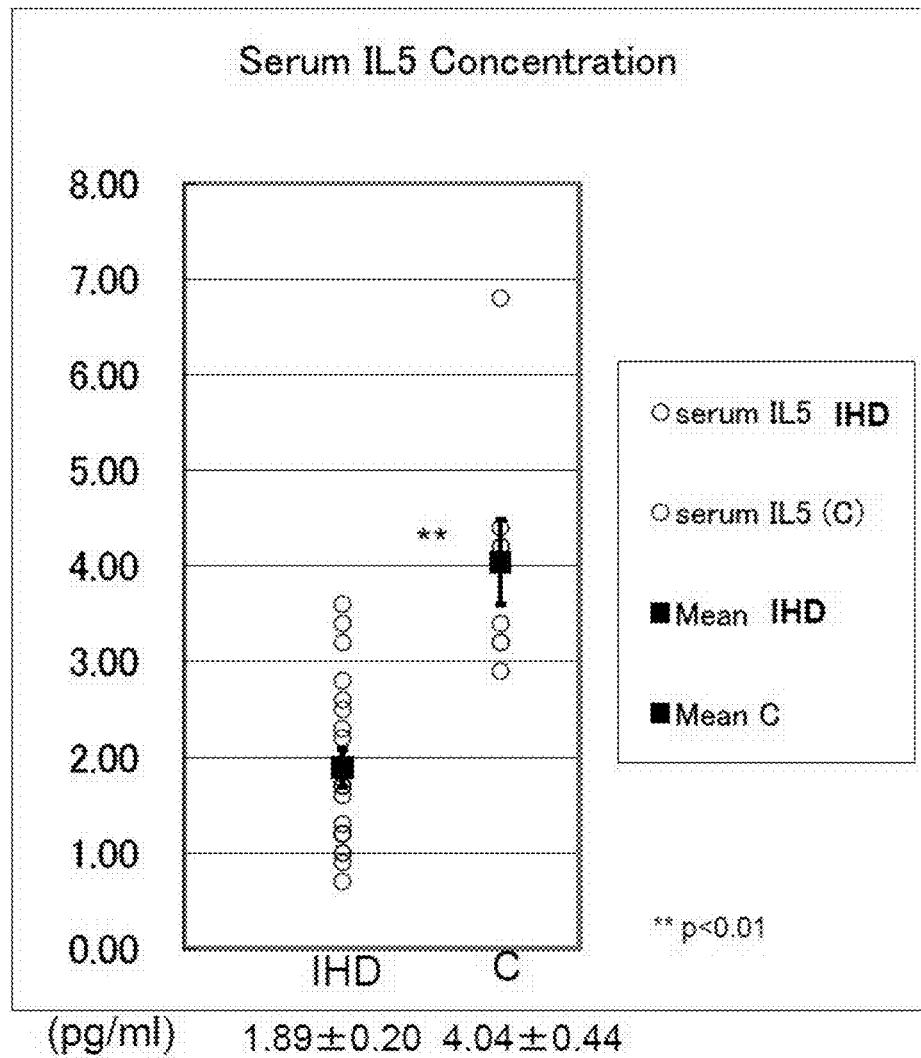
FIG. 13 Measurement results of concentrations of IL-5 in sera from patients with ischemic heart disease (in the figure, "C" indicates no addition of IL-5).

FIG. 13 shows the results of the above-mentioned measurement.

As shown in FIG. 13, it was confirmed that the concentrations of IL-5 in the sera from the patients with ischemic heart disease as patients with arteriosclerosis significantly lowered.

Thus, an autoimmune disease, in particular, arteriosclerosis can be inspected by detecting the concentration of IL-5 in a serum from a patient.

Example 11

Preparation of Receiver Operating Characteristic Curve of Anti-IL-5 Antibody Titer Based on the results of Examples 9 and 10 above, a receiver operating characteristic curve of the antibody titer of an anti-IL-5 antibody was prepared.

Figure 14:
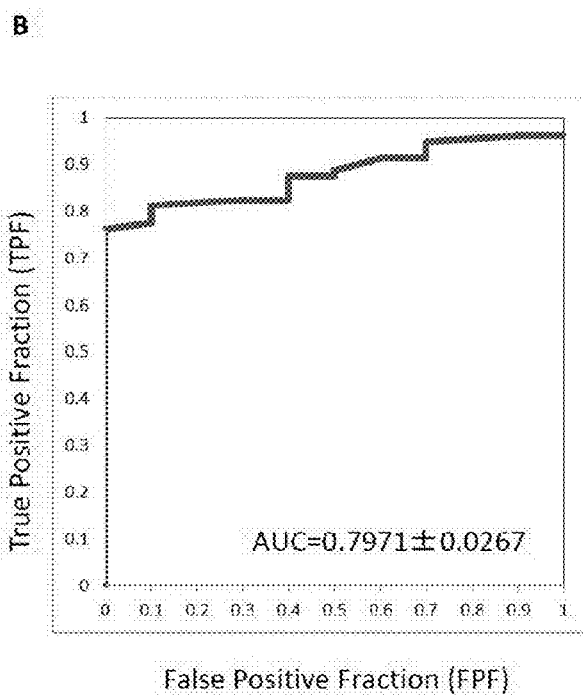
FIG. 14 A receiver operating characteristic curve of antibody titers of the anti-IL-5 antibody.

As shown in FIG. 14, when a cutoff value is set to 1.19 to 1.21, the sensitivity and specificity of the antibody titer of the anti-IL-5 antibody are as follows: sensitivity: about 81.3%; and specificity: 90%.

Thus, it was confirmed that the examination of an autoimmune disease, in particular, arteriosclerosis involving detecting the antibody titer of the IL-5 antibody in a serum from a patient had high sensitivity and specificity.

INDUSTRIAL APPLICABILITY

In the present invention, the means for analyzing a protein involved in an autoimmune disease, in particular, arteriosclerosis with high sensitivity and high efficiency can be provided.

The invention claimed is:

1. A method for assessing the presence of arteriosclerosis in a subject suspected of having arteriosclerosis, the method comprising:
    (a) obtaining a serum sample from the subject;
    (b) measuring an antibody titer of an autoantibody against an IL-5 polypeptide present in the sample, wherein the IL-5 polypeptide consists of a polypeptide sequence selected from the group consisting of SEQ ID NO:2 and SEQ ID NO:3, and wherein the IL-5 polypeptide is obtained by Cell Free Protein Synthesis System using wheat germ; and
    (c) comparing the antibody titer of the autoantibody against IL-5 in the serum from the subject with an antibody titer of an autoantibody against IL-5 in a serum sample from a healthy subject;
    wherein a significant increase in the titer of the autoantibody against IL-5 in the serum sample from the subject as compared to the titer of the autoantibody against IL-5 in the serum sample from the healthy subject is indicative of the presence of arteriosclerosis in the subject.

2. The examination method according to claim 1, wherein the arteriosclerosis comprises atherosclerosis.

* * * * *

SEQUENCE LISTING

<160> NUMBER OF SEQ ID NOS: 3

<210> SEQ ID NO 1
<211> LENGTH: 134
<212> TYPE: PRT
<213> ORGANISM: Homo sapiens
<220> FEATURE:
<223> OTHER INFORMATION: full length IL-5

<400> SEQUENCE: 1

Met Arg Met Leu Leu His Leu Ser Leu Leu Ala Leu Gly Ala Ala Tyr
1               5                   10                  15

Val Tyr Ala Ile Pro Thr Glu Ile Pro Thr Ser Ala Leu Val Lys Glu
            20                  25                  30

Thr Leu Ala Leu Leu Ser Thr His Arg Thr Leu Leu Ile Ala Asn Glu
        35                  40                  45

Thr Leu Arg Ile Pro Val Pro Val His Lys Asn His Gln Leu Cys Thr
    50                  55                  60

Glu Glu Ile Phe Gln Gly Ile Gly Thr Leu Glu Ser Gln Thr Val Gln
65                  70                  75                  80

Gly Gly Thr Val Glu Arg Leu Phe Lys Asn Leu Ser Leu Ile Lys Lys
                85                  90                  95

Tyr Ile Asp Gly Gln Lys Lys Lys Cys Gly Glu Glu Arg Arg Arg Val
            100                 105                 110

Asn Gln Phe Leu Asp Tyr Leu Gln Glu Phe Leu Gly Val Met Asn Thr
        115                 120                 125

Glu Trp Ile Ile Glu Ser
    130

<210> SEQ ID NO 2
<211> LENGTH: 115
<212> TYPE: PRT
<213> ORGANISM: Homo sapiens
<220> FEATURE:
<223> OTHER INFORMATION: partial sequence IL-5(IL-5(20-135))

<400> SEQUENCE: 2

Ile Pro Thr Glu Ile Pro Thr Ser Ala Leu Val Lys Glu Thr Leu Ala
1               5                   10                  15

Leu Leu Ser Thr His Arg Thr Leu Leu Ile Ala Asn Glu Thr Leu Arg
            20                  25                  30

Ile Pro Val Pro Val His Lys Asn His Gln Leu Cys Thr Glu Glu Ile
        35                  40                  45

Phe Gln Gly Ile Gly Thr Leu Glu Ser Gln Thr Val Gln Gly Gly Thr
    50                  55                  60

Val Glu Arg Leu Phe Lys Asn Leu Ser Leu Ile Lys Lys Tyr Ile Asp
65                  70                  75                  80

Gly Gln Lys Lys Lys Cys Gly Glu Glu Arg Arg Arg Val Asn Gln Phe
                85                  90                  95

Leu Asp Tyr Leu Gln Glu Phe Leu Gly Val Met Asn Thr Glu Trp Ile
            100                 105                 110

Ile Glu Ser
        115

<210> SEQ ID NO 3
<211> LENGTH: 71
<212> TYPE: PRT
<213> ORGANISM: Homo sapiens
<220> FEATURE:

```
<223> OTHER INFORMATION: partial sequence IL-5(IL-5(64-135))

<400> SEQUENCE: 3

Thr Glu Glu Ile Phe Gln Gly Ile Gly Thr Leu Glu Ser Gln Thr Val
1               5                   10                  15

Gln Gly Gly Thr Val Glu Arg Leu Phe Lys Asn Leu Ser Leu Ile Lys
            20                  25                  30

Lys Tyr Ile Asp Gly Gln Lys Lys Lys Cys Gly Glu Glu Arg Arg Arg
        35                  40                  45

Val Asn Gln Phe Leu Asp Tyr Leu Gln Glu Phe Leu Gly Val Met Asn
    50              55                  60

Thr Glu Trp Ile Ile Glu Ser
65              70
```